United States Patent
Hashida et al.

(10) Patent No.: US 11,268,956 B2
(45) Date of Patent: Mar. 8, 2022

(54) METHOD FOR PRODUCING ANTIBODY REAGENT

(71) Applicant: SYSMEX CORPORATION, Kobe (JP)

(72) Inventors: Seiichi Hashida, Tokushima (JP); Aya Morimoto, Hyogo (JP); Toshihiro Watanabe, Hyogo (JP); Takahiro Yamagaito, Tokyo (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 15/635,385

(22) Filed: Jun. 28, 2017

(65) Prior Publication Data

US 2018/0003707 A1 Jan. 4, 2018

(30) Foreign Application Priority Data

Jun. 30, 2016 (JP) .............................. JP2016-129759

(51) Int. Cl.
| | |
|---|---|
| *G01N 33/543* | (2006.01) |
| *G01N 33/535* | (2006.01) |
| *G01N 33/576* | (2006.01) |
| *C07K 16/08* | (2006.01) |
| *C07K 16/00* | (2006.01) |

(52) U.S. Cl.
CPC ....... *G01N 33/54393* (2013.01); *C07K 16/00* (2013.01); *C07K 16/082* (2013.01); *G01N 33/535* (2013.01); *G01N 33/54306* (2013.01); *G01N 33/5761* (2013.01); *G01N 2333/02* (2013.01)

(58) Field of Classification Search
CPC .. C07K 16/00; C07K 16/082; G01N 2333/02; G01N 33/535; G01N 33/54306; G01N 33/54393; G01N 33/5761; G01N 33/5764
See application file for complete search history.

(56) References Cited

U.S. PATENT DOCUMENTS

| | | | | |
|---|---|---|---|---|
| 4,659,678 A | * | 4/1987 | Forrest ............. | G01N 33/54306 436/512 |
| 4,855,057 A | | 8/1989 | Ohnishi et al. | |
| 10,352,937 B2 | * | 7/2019 | Yamagaito ......... | G01N 33/5764 |
| 2015/0330982 A1 | * | 11/2015 | Yamagaito ......... | G01N 33/5761 435/5 |
| 2017/0030899 A1 | * | 2/2017 | Watanabe ........ | G01N 33/54306 |
| 2018/0348212 A1 | * | 12/2018 | Watanabe ............. | G01N 33/53 |

FOREIGN PATENT DOCUMENTS

| | | | |
|---|---|---|---|
| EP | 1 767 942 A1 | | 3/2007 |
| EP | 3315969 A1 | * | 5/2018 |
| JP | H08-304397 A | | 11/1996 |
| JP | 3667434 B2 | | 7/2005 |
| JP | 2008-216237 A | * | 9/2008 |

OTHER PUBLICATIONS

Machine translation of JP 2008-216237, published Sep. 18, 2008.*
English Abstractor JP 2008-216237, published Sep. 18, 2008.*
Kumiko Ohne, et al., "Clinical Evaluation of a Newly Developed High-Sensitive Detection of Hepatitis B Virus Surface Antigen by a Semi-Automated Immune Complex Transfer Chemiluminescent Enzyme Immunoassay", Rinsho Byori, 2013, pp. 787-794, vol. 61.
Kazuhiko Takeda, et al., "Highly Sensitive Detection of Hepatitis B Virus Surface Antigen by Use of a Semiautomated Immune Complex Transfer Chemiluminescence Enzyme Immunoassay", Journal of Clinical Microbiology, 2013, pp. 2238-2244, vol. 51, No. 7.
Eiji Ishikawa et al., "Principle and Applications of Ultrasensitive Enzyme Immunoassay (Immune Complex Transfer Enzyme Immunoassay) for Antibodies in Body Fluids", Journal of Clinical Laboratory Analysis vol. 7, No. 6, pp. 376-393, 1993, XP009055290.
Takeshi Namiki et al., "A novel approach to enhance antibody sensitivity and specificity by peptide cross-Tinking", Analytical Biochemistry, Elsevier, vol. 383, No. 2, 2008, pp. 265-269, XP025585792.
The Japanese Office Action dated Apr. 22, 2020 in a counterpart Japanese patent application No. 2016-129759.
The Japanese Office Action dated Jan. 7, 2020 in a counterpart Japanese patent application No. 2016-129759.
The European Office Action dated Jan. 17, 2020 in a counterpart European patent application No. 17178811.0.

* cited by examiner

*Primary Examiner* — Galina M. Yakovleva
(74) *Attorney, Agent, or Firm* — Sughrue Mion, PLLC

(57) ABSTRACT

Disclosed is a method for producing an antibody reagent for detecting a test substance in a sample by an immune complex transfer method. The method comprises the steps of: bringing an antibody solution comprising a labeled antibody capable of binding to the test substance into contact with a solid phase used in the immune complex transfer method; and separating the solid phase and the antibody solution to prepare the antibody reagent from the antibody solution.

4 Claims, 4 Drawing Sheets

METHOD FOR PRODUCING ANTIBODY REAGENT

CROSS REFERENCE TO RELATED APPLICATIONS

This application claims priority from prior Japanese Patent Application No. 2016-129759, filed on Jun. 30, 2016, entitled "ANTIBODY REAGENT FOR DETECTING TEST SUBSTANCE BY IMMUNE COMPLEX TRANSFER METHOD, METHOD FOR PRODUCING THE SAME, AND USE OF THE SAME", the entire contents of which are incorporated herein by reference.

TECHNICAL FIELD

The present invention relates to a method for producing an antibody reagent for detecting a test substance in a sample by an immune complex transfer method.

BACKGROUND

The immunoassay makes it possible to detect a test substance with high accuracy by utilizing a specific antigen-antibody reaction between a test substance in a sample and an antibody for detection which binds to the test substance. However, it is known that, in the immunoassay, substances other than the test substance in the sample cause non-specific reactions. Such non-specific reactions raise the background signal, resulting in the reduction of sensitivity and specificity of the immunoassay.

Conventionally, various measures have been attempted in order to suppress non-specific reactions in the immunoassay. For example, U.S. Pat. No. 536,686 discloses adding as a blocking agent a protein such as casein having an average molecular weight and an isoelectric point within a predetermined range to a sample. JP Patent No. 3667434 discloses adding an antibody as a non-specific reaction suppressive that lost its original reactivity obtained by heat treatment of the same antibody as that used for a labeled antibody to a sample. JP 5005511 discloses adding non-magnetic particles made of a material the surface of which is the same as the magnetic particle, to a sample in an immunoassay using magnetic particles as a solid phase in order to prevent a substance other than a test substance in a sample from non-specifically binding to the magnetic particles. EP 1767942 A1 discloses using an enzyme-labeled antibody in which the number of bonds of the enzyme to the antibody for detection is limited to a predetermined ratio in order to suppress non-specific reaction by human anti-mouse antibody present in human blood.

SUMMARY OF THE INVENTION

The scope of the present invention is defined solely by the appended claims, and is not affected to any degree by the statements within this summary.

A sample to be subjected to an immunoassay, particularly a biological sample, contains various substances besides a test substance. Therefore, in the immunoassay, the main objective is to suppress a non-specific reaction by substances other than the test substance derived from the sample. In fact, all the above-described conventional techniques are techniques for preventing a non-specific adsorption or binding of a substance other than a test substance in a sample to an antibody for detection or a solid phase. However, the present inventors have found that substances which cause a non-specific reaction also exist in reagents used for measurement. That is, the inventors have found that a problem occurs in the immune complex transfer measurement method, i.e. a labeled antibody capable of binding to a test substance binds non-specifically to a solid phase to generate a non-specific signal. In other words, the inventors have found a problem that not all of the molecules of the labeled antibody contained in the reagent uniformly form a specific bond with the test substance, but among the antibody molecules, some of the molecules not only bind specifically to the test substance, but also bind non-specifically to the solid phase.

The present inventors have found that non-specific signals due to the labeled antibody can be reduced by pretreatment in which an antibody solution containing a labeled antibody capable of binding to a test substance is brought into contact with a solid phase, and have completed the present invention based on the finding.

The present invention provides a method for producing an antibody reagent for detecting a test substance in a sample by an immune complex transfer method, comprising the steps of:

bringing an antibody solution comprising a labeled antibody capable of binding to the test substance into contact with a solid phase used in the immune complex transfer method and separating the solid phase and the antibody solution to prepare the antibody reagent from the antibody solution, wherein:

the labeled antibody comprises a label, a binding substance is immobilized on the solid phase, in the immune complex transfer method, a capture antibody that specifically binds to the test substance is used, and the capture antibody comprises a binding partner capable of specifically binding to the binding substance.

DETAILED DESCRIPTION OF THE PREFERRED EMBODIMENTS

[1. Antibody Reagent]

Figure 1:
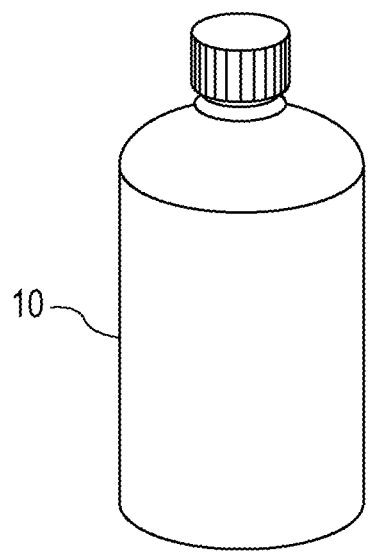
FIG. 1 is a schematic view showing an example of an antibody reagent of the present embodiment.

The antibody reagent of the present embodiment (hereinafter also simply referred to as "antibody reagent") contains a labeled antibody capable of binding to a test substance, and is suitable for detecting a test substance in a sample by an immune complex transfer method.

Here, the immune complex transfer method (hereinafter also referred to as "ICT method") is a method in which an immune complex comprising at least a labeled antibody contained in the antibody reagent of the present embodiment, a test substance, and a capture substance capable of binding to the test substance is formed on a solid phase and then the immune complex is transferred to another solid phase.

The ICT method itself is known in the art. In a general ICT method, using a labeled antibody (a labeled antibody for detection) for detecting a test substance and an antibody (a capture antibody) for capturing the test substance, the test substance is detected by the following procedure.

First, an immune complex containing a labeled antibody for detection, a test substance, and a capture antibody is formed on a first solid phase. In this immune complex, the test substance is sandwiched between the labeled antibody for detection and the capture antibody. The immune complex is then transferred from the first solid phase to a second solid phase different from the first solid phase. Then, a signal based on the labeled antibody for detection contained in the immune complex on the second solid phase is measured, and the test substance is detected based on the measured value of the signal. In the ICT method, the first solid phase is removed when the immune complex is transferred to the second solid phase. At this time, impurities non-specifically bound to the first solid phase are simultaneously removed, so that non-specific signals are reduced.

The antibody reagent of the present embodiment may be used for detecting a test substance in a sample by an immunoassay applying the ICT method. As such a measurement method, for example, an immune complex transfer-enzyme immunoassay (ICT-EIA method) which is an ICT method using an enzyme-labeled antibody, an immune complex transfer-chemiluminescent enzyme immunoassay (ICT-CLEIA method) which is an ICT method using an antibody labeled with an enzyme that catalyzes a reaction causing chemiluminescence, and the like can be mentioned.

The sample targeted by the antibody reagent of the present embodiment is not particularly limited as far as it can contain a test substance. Examples of the sample include biological samples such as blood, plasma, serum, lymph fluid, solubilized liquid of cells or tissues, excreta such as urine and feces, and environmental samples such as river water, seawater, and soil.

The kind of the test substance is not particularly limited as long as an antibody capable of binding to the test substance is present or can be produced. That is, any substance having antigenicity can be a test substance. Examples of the test substance include, but are not limited to, proteins, peptides, nucleic acids, physiologically active substances, vesicles, bacteria, viruses, haptens, therapeutic drugs, metabolites of therapeutic drugs and the like. Antibodies can also be test substances. Proteins include not only naturally occurring proteins but also non-natural proteins such as recombinant proteins. Peptides include not only polypeptides having a large number of amino acid residues but also oligopeptides having a small number of amino acid residues such as dipeptides and tripeptides. Nucleic acids include not only naturally occurring nucleic acids but also artificially synthesized nucleic acids such as nucleic acid analogs. Polysaccharides also include sugar chains present on the surface of cells or proteins, and lipopolysaccharides which are outer membrane components of bacteria. Examples of the physiologically active substance include, but are not limited to, cell growth factors, differentiation inducing factors, cell adhesion factors, enzymes, cytokines, hormones, sugar chains and lipids. The vesicle is not particularly limited as long as it is a vesicle composed of a membrane. The vesicle may contain a liquid phase therein. Examples of the vesicle include extracellular vesicles such as exosomes, microvesicles and apoptotic bodies, and artificial vesicles such as liposomes.

The labeled antibody contained in the antibody reagent of the present embodiment and capable of binding to the test substance is not particularly limited as long as it is an antibody which binds to the test substance by a specific antigen-antibody reaction to the test substance and is labeled with a labeling substance. This labeled antibody corresponds to a labeled antibody for detection in the ICT method. The labeled antibody itself can be obtained by labeling an antibody capable of binding to a test substance with a labeling substance known in the art. The antibody itself capable of binding to the test substance can be obtained by an antibody production method known in the art.

The antibody reagent of the present embodiment may contain one type of labeled antibody or may contain two or more types of labeled antibodies capable of binding to mutually different test substances. In the case where the antibody reagent contains two or more types of labeled antibodies, it is preferable that each labeled antibody is obtained by labeling with a labeling substance which can detect signals distinguishable from each other. As such a labeling substance, for example, a combination of fluorescent dyes capable of generating fluorescence having different wavelengths or intensities to be distinguishable from each other can be mentioned.

The type of antibody used for the labeled antibody may be a monoclonal antibody or a polyclonal antibody. The origin of the antibody is not particularly limited, and antibodies derived from any mammal such as mouse, rat, hamster, rabbit, goat, horse, camel and the like may be used. In addition, the isotype of the antibody may be any of IgG, IgM, IgE, IgA and the like, but is preferably IgG. For the labeled antibody, fragments of antibodies and derivatives thereof may be used, including, for example, Fab fragments, F(ab')2 fragments, single chain antibodies (scFc) and the like.

As the labeling substance, a substance which itself generates a signal (hereinafter also referred to as "signal generating substance") or a substance which can generate a detectable signal by catalyzing the reaction of another substance can be used. As the signal generating substance, there can be mentioned a fluorescent substance, a radioactive isotope and the like. As a substance that catalyzes the reaction of other substances and generates a detectable signal, an enzyme can be mentioned. Preferred labeling substances are enzymes and fluorescent substances. Examples of the enzyme include alkaline phosphatase, peroxidase, β-galactosidase, glucosidase, polyphenol oxidase, tyrosinase, acid phosphatase, luciferase and the like. Examples of the fluorescent substance include fluorescent dyes such as fluorescein isothiocyanate (FITC), rhodamine, Alexa Fluor (registered trademark), and cyanine dyes, and fluorescent proteins such as GFP. Examples of the radioactive isotope include $^{125}$I, $^{35}$S, $^{32}$P, $^{14}$C, and the like. Among these, enzymes are preferable, and alkaline phosphatase, peroxidase and β-galactosidase are particularly preferable.

The antibody reagent of the present embodiment is characterized in that the ratio of the number of molecules of the labeled antibody non-specifically bound to the solid phase used in the immune complex transfer method (hereinafter also referred to as "ratio of non-specific antibody") to the number of molecules of the labeled antibody contained in the antibody reagent, is about $3.34 \times 10^{-7}$ or less. Labeled antibodies that bind non-specifically to the solid phase used in the ICT method are responsible for the generation of non-specific signals. In the antibody reagent of the present embodiment, since the labeled antibody that non-specifically binds to the solid phase is reduced to the above ratio, non-specific signal can be suppressed to a low level in the ICT method. As used herein, "non-specifically binding" means a binding not involving an antigen-antibody reaction, and examples thereof include physical adsorption, electrostatic interaction, and the like.

In the present embodiment, the ratio of the number of molecules of the labeled antibody non-specifically bound to the solid phase used in the ICT method to the number of molecules of the labeled antibody contained in the antibody reagent is preferably about $3.34 \times 10^{-7}$ or less, more preferably about $2.81 \times 10^{-7}$ or less. In a further embodiment, the ratio of the number of molecules of the labeled antibody non-specifically bound to the solid phase used in the ICT method to the number of molecules of the labeled antibody contained in the antibody reagent is $3.34 \times 10^{-7}$ or less, more preferably $2.81 \times 10^{-7}$ or less.

The ratio of the non-specific antibody may be calculated based on a value reflecting the number of molecules of the labeled antibody. Such values include, for example, the concentration or amount of a protein in the antibody reagent, the concentration or amount of a labeling substance in the antibody reagent, the measured value of a signal based on the labeled antibody, and the like. The ratio of the non-specific antibody is a value that reflects the number of molecules of the labeled antibody contained in the antibody reagent and divides a value that reflects the number of molecules of the labeled antibody non-specifically binding to the solid phase used in the ICT method. At this time, the unit of the value reflecting the number of molecules of the labeled antibody contained in the antibody reagent is preferably the same as the unit of the value reflecting the number of molecules of the labeled antibody non-specifically binding to the solid phase used in the ICT method.

The value reflecting the number of molecules of the labeled antibody contained in the antibody reagent may be either the concentration or amount of the protein, the concentration or amount of the labeling substance, or the measured value of the signal based on the labeled antibody. Since the protein component contained in the antibody reagent of the present embodiment is mainly a labeled antibody, the concentration and amount of the protein in the antibody reagent reflects the number of molecules of the labeled antibody contained in the antibody reagent. The concentration and amount of the protein contained in the antibody reagent may be measured by a protein quantification method known in the art.

Since the labeling substance is bound or immobilized onto the antibody in the labeled antibody, the concentration and amount of the labeling substance in the antibody reagent reflects the number of molecules of the labeled antibody contained in the antibody reagent. The concentration or amount of the labeling substance contained in the antibody reagent may be measured by a method known in the art depending on the type of the labeling substance. Alternatively, the concentration and amount of the labeling substance in the antibody reagent may be calculated from the amount of the labeling substance used in preparing the labeled antibody.

Since the amount or intensity of the signal based on the labeled antibody varies depending on the number of molecules of the labeled antibody contained in the antibody reagent used, the measured value of the signal based on the labeled antibody contained in the predetermined amount of the antibody reagent reflects the number of molecules of the labeled antibody contained in that amount of the antibody reagent. The amount or intensity of the signal based on the labeled antibody may be measured by measuring a signal based on the labeled antibody contained in a predetermined amount of the antibody reagent in a known measurement method according to the type of the labeling substance.

When the concentration of the labeled antibody is high, a signal based on the labeled antibody contained in the diluted antibody reagent may be measured. In this case, the signal value based on the labeled antibody contained in the antibody reagent before dilution may be calculated by multiplying the measurement value of the obtained signal by the dilution ratio.

In the present embodiment, the coefficient for converting the measured value of the signal into the amount of the protein or the labeling substance (hereinafter also referred to as "conversion coefficient") may be calculated from the amount of the protein or the labeling substance in a predetermined amount of the antibody reagent and the measured value of the signal based on the labeled antibody contained in the predetermined amount of the antibody reagent. This coefficient can be used to obtain a value that reflects the number of molecules of the labeled antibody non-specifically binding to the solid phase used in the ICT method.

As a value reflecting the number of molecules of a labeled antibody that non-specifically binds to a solid phase used in the ICT method, it is preferable to obtain a measured value of a signal based on such a labeled antibody. For example, when the solid phase is a magnetic particle, a measured value of a signal based on a labeled antibody that non-specifically binds to the solid phase can be obtained as follows. First, a predetermined amount of the antibody reagent of the present embodiment and magnetic particles are mixed and incubated at 37 to 42° C. for 60 to 600 seconds. The amount of the antibody reagent and the solid phase is not particularly limited and may be an amount that is used when conducting a conventional detection assay. Next, in order to remove the free component (unreacted labeled antibody) in the obtained mixture, the magnetic particles are recovered by a magnet or a magnetic collector and then washed. Then, the magnetic particles are recovered, and a signal based on the labeled antibody non-specifically bound to the magnetic particles is measured to obtain a measured value of the signal. In the case where the conversion coefficient is acquired, the amount of the protein or the labeling substance may be calculated as a value reflecting the number of molecules of the labeled antibody non-specifically bound to the solid phase, from the measured value of the signal and this coefficient.

An example of the antibody reagent of the present embodiment is shown in FIG. 1. In FIG. 1, a reference numeral 10 denotes a first container containing an antibody reagent. The form of the antibody reagent of the present embodiment may be liquid or powder (lyophilized product). When the antibody reagent is a liquid, the solvent is not particularly limited as long as it can dissolve and store the labeled antibody. Examples of the solvent include water, physiological saline, phosphate buffer (PBS), Good's buffer and the like. Examples of Good's buffers include MES, Bis-Tris, ADA, PIPES, Bis-Tris-Propane, ACES, MOPS, MOPSO, BES, TES, HEPES, HEPPS, Tricine, Tris, Bicine, and TAPS.

The antibody reagent of the present embodiment may contain known additives as necessary. Examples of the additives include protein stabilizers such as bovine serum albumin (BSA), antiseptics such as sodium azide, inorganic salts such as sodium chloride, and the like.

In recent years, it has been known that when an immunosuppressive agent is used for rheumatism patients or cancer patients who have been infected with hepatitis B virus (HBV), HBV is reactivated to cause severe hepatitis. To prevent such fulminant hepatitis, it is important to detect HBV reactivation at an early stage. For that purpose, it is necessary to conduct an examination capable of detecting an HBs antigen, which is an antigen present in the HBV envelope, with high sensitivity. Since the antibody reagent of the present embodiment can realize an ICT method with high detection sensitivity, it is suitably used for the detection of HBs antigen. Therefore, the antibody reagent of the present embodiment for detecting an HBs antigen in a sample by the ICT method contains a labeled anti-HBs antibody, and the ratio of the non-specific antibody in the antibody reagent is about $3.34 \times 10^{-7}$ or less, preferably $3.34 \times 10^{-7}$ or less.

The scope of the present disclosure includes the use of a labeled antibody capable of binding to the test substance for producing an antibody reagent for detecting a test substance in a sample by an immune complex transfer method, i.e. the use of a labeled antibody wherein the ratio of the number of molecules of the labeled antibody non-specifically bound to the solid phase used for the immune complex transfer method is about $3.34 \times 10^{-7}$ or less, preferably $3.34 \times 10^{-7}$ or less.

[2. Reagent Kit]

Figure 2A:
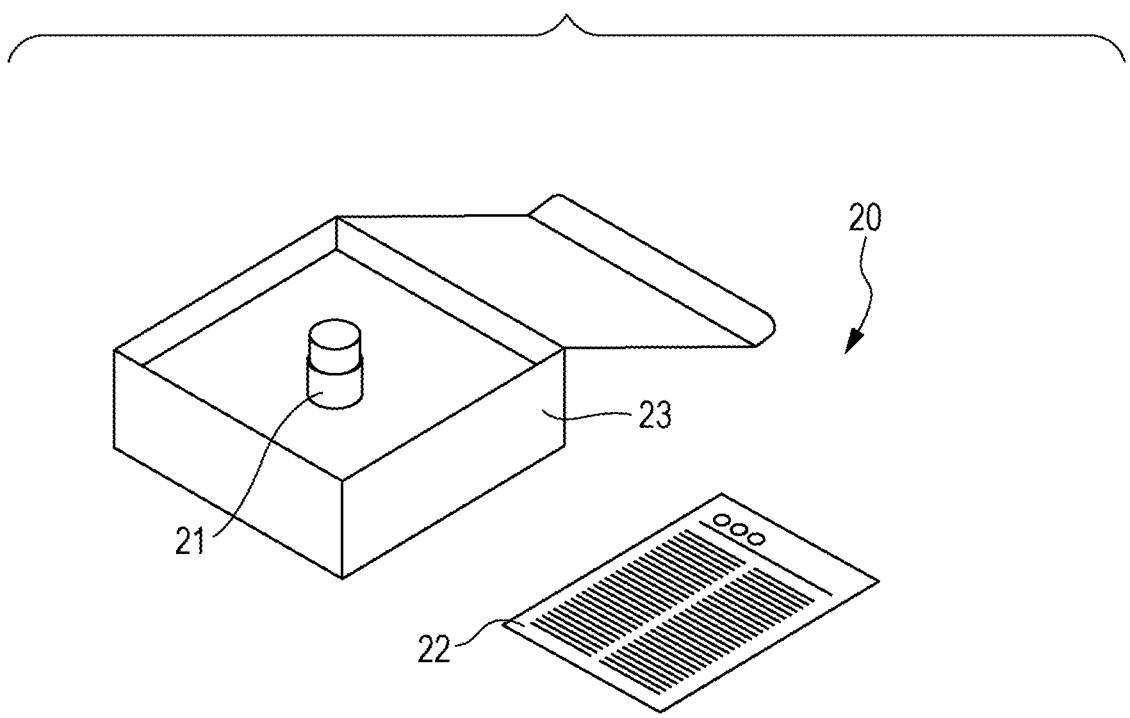
FIG. 2A is a schematic view showing an example of an antibody reagent of the present embodiment provided in the form of a reagent kit.

The antibody reagent of the present embodiment may be provided to the user in the form of a reagent kit in which a container containing the antibody reagent is packed in a box. This box may contain a package insert of the reagent. In this package insert, for example, it is preferable to describe the composition of the antibody reagent, the detection protocol of the test substance, and the like. An example of the antibody reagent provided in the form of a reagent kit is shown in FIG. 2A. In FIG. 2A, a reference numeral 20 denotes a reagent kit, a reference numeral 21 denotes a first container accommodating the antibody reagent of the present embodiment, a reference numeral 22 denotes a package insert, and a reference numeral 23 denotes a packaging box.

In the present embodiment, in addition to the antibody reagent described above, a reagent kit further including various reagents used for detecting a test substance in a sample by an immune complex transfer method may be provided to the user. That is, the scope of the present disclosure includes a reagent kit (hereinafter also simply referred to as "reagent kit") for detecting a test substance in a sample by an immune complex transfer method. The reagent kit of the present embodiment includes the antibody reagent of the present embodiment, a reagent containing a capture substance capable of binding to a test substance, a releasing agent, a first solid phase, and a second solid phase. The antibody reagent of the present embodiment is as described above.

Figure 2B:
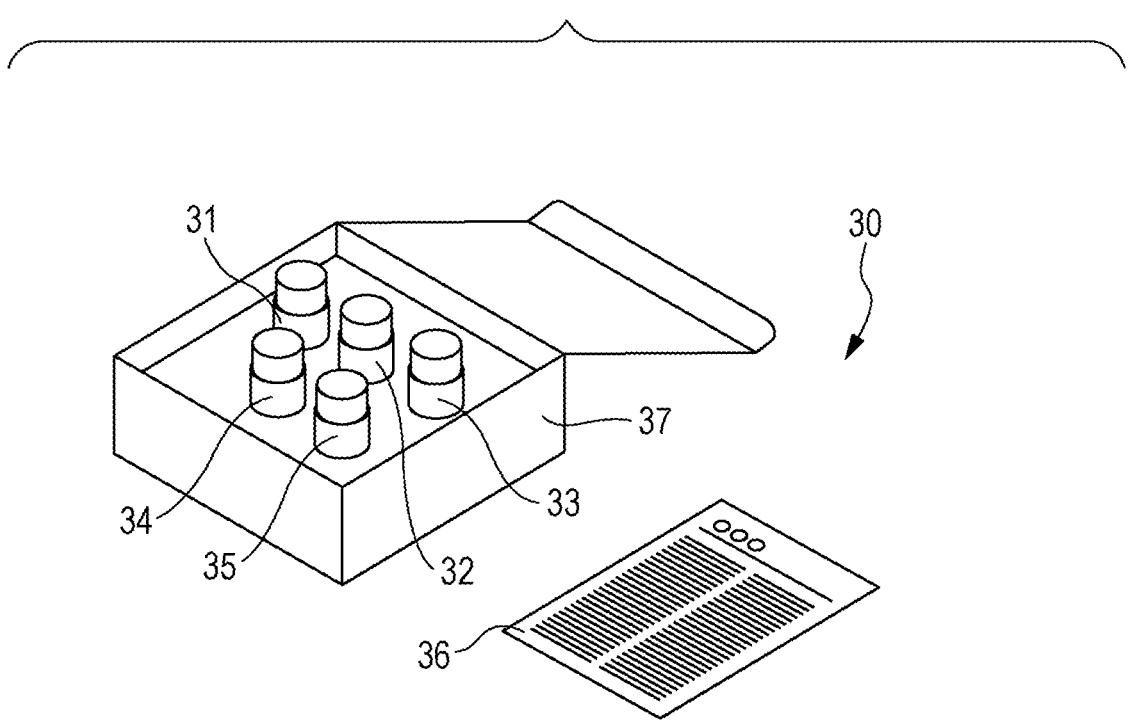
FIG. 2B is a schematic view showing an example of a reagent kit of the present embodiment.

An example of the reagent kit of the present embodiment is shown in FIG. 2B. In FIG. 2B, a reference numeral 30 denotes a reagent kit, a reference numeral 31 denotes a first container containing the antibody reagent of the present embodiment, a reference numeral 32 denotes a second container containing a reagent containing a capture substance capable of binding to the test substance, a reference numeral 33 denotes a third container containing a releasing agent, a reference numeral 34 denotes a fourth container containing a first solid phase as a particle, a reference numeral 35 denotes a fifth container containing a second solid phase as a particle, a reference numeral 36 denotes a package insert, and a reference numeral 37 denotes a packaging box.

A capture substance capable of binding to a test substance (hereinafter also simply referred to as "capture substance") is a substance that specifically binds to a test substance and has a first binding partner capable of binding to a first binding substance and a second binding partner capable of binding to a second binding substance. The binding substance and the binding partner will be described later. It is preferable that the capture substance binds to a site different from the site to which the labeled antibody contained in the antibody reagent of the present embodiment binds in the test substance. Such a capture substance does not cause competitive inhibition against the labeled antibody in the antigen-antibody reaction between the test substance and the labeled antibody. In the ICT method, an immune complex containing a test substance sandwiched between a labeled antibody and a capture substance can be obtained.

The type of the capture substance is not particularly limited and can be appropriately selected depending on the test substance. Examples of the types of the capture substances include, for example, antibodies and fragments thereof, aptamers, Affibody (registered trademark), lectins, nucleic acids and the like. Since lectin binds to a sugar chain, it can be used as a capture substance for a test substance having a sugar chain. In the case where the test substance is a nucleic acid, if a nucleic acid is used as a capture substance, the test substance can be captured utilizing formation of a complementary base pair. Among them, antibodies are preferred as the capture substance. The details of the type and origin of the antibody are the same as those described for the labeled antibody. An antibody as a capture substance is herein also referred to as "capture antibody".

The first solid phase is a solid phase for capturing an immune complex comprising a labeled antibody, a test substance and a capture substance. The solid phase material can be selected from organic polymer compounds, inorganic compounds, biopolymers and the like. Examples of the organic polymer compound include latex, polystyrene, polypropylene and the like. Examples of the inorganic compound include magnetic materials (iron oxide, chromium oxide, cobalt, ferrite, etc.), silica, alumina, glass and the like. Examples of the biopolymer include insoluble agarose, insoluble dextran, gelatin, cellulose and the like. Two or more of these may be used in combination. The shape of the solid phase is not particularly limited, and examples thereof include particles, microplates, microtubes, test tubes, and the like. Particles among them are preferred. In the case where the ICT method is performed by a fully automated immunoassay system, it is particularly preferable that the first solid phase is magnetic particles.

In the present embodiment, a first binding substance for immobilizing a capture substance in an immune complex is immobilized on the first solid phase. In the present embodiment, since the capture substance has a first binding partner capable of binding to the first binding substance, the capture substance in the immune complex is immobilized on the first solid phase by the binding formed between the first binding partner and the first binding substance immobilized on the first solid phase. Thereby, the immune complex is captured on the first solid phase.

The first binding substance and the first binding partner are not particularly limited as long as a substance capable of dissociating the bond between the first binding substance and the first binding partner is present. Examples of such combination of the first binding substance and the first binding partner include a combination of biotin and avidin or avidin-like protein, hapten and anti-hapten antibody, nickel and histidine tag, glutathione and glutathione-S-transferase. The avidin-like protein is a protein having high affinity for biotin as with avidin, and examples thereof include streptavidin, Tamavidin (registered trademark), and the like. Among them, biotin and avidin or avidin-like protein, hapten and anti-hapten antibody are preferred. Preferably, the first binding substance is a hapten and the first binding partner is an anti-hapten antibody. More preferably, the first binding substance is a dinitrophenyl (DNP) group and the first binding partner is an antibody (anti-DNP antibody) specifically binding to the DNP group.

The releasing agent is a reagent capable of dissociating the bond between the first binding substance and the first binding partner. By adding a releasing agent, the immune complex immobilized on the first solid phase is released from the first solid phase. The releasing agent can be appropriately selected according to the combination of the first binding substance and the first binding partner. For example, the binding between biotin and avidin or an avidin-like protein can be dissociated by the excessive addition of biotin. The binding between the hapten and the anti-hapten antibody can be dissociated by the addition of a hapten. The binding between nickel and histidine tag can be dissociated by the addition of an imidazole. The binding between glutathione and glutathione-S-transferase can be dissociated by the addition of a reduced glutathione. When the first binding substance is a DNP group and the first binding partner is an anti-DNP antibody, the releasing agent is preferably a DNP derivative. As the DNP derivative, for example, amino acids modified with DNP and the like can be mentioned, among which N-(2,4-dinitrophenyl)-L-lysine (hereinafter also referred to as "DNP lysine") is particularly preferable.

The second solid phase is a solid phase for capturing the immune complex released from the first solid phase by using a releasing agent. The details of the material and shape of the solid phase are the same as those described for the first solid phase. In the case where the ICT method is carried out by a fully automated immunoassay apparatus, it is particularly preferable that the second solid phase is a magnetic particle.

In the present embodiment, a second binding substance for immobilizing the capture substance in the immune complex is immobilized on the second solid phase. In the present embodiment, since the capture substance has a second binding partner capable of binding to the second binding substance, the capture substance in the immune complex is immobilized on the second solid phase by binding the second binding partner to the second binding substance immobilized on the second solid phase. Thereby, the immune complex is captured by the second solid phase.

The combination of the second binding substance and the second binding partner can be appropriately selected from the combination of the first binding substance and the first binding partner as long as the combination of the second binding substance and the second binding partner is different from the combination of the first binding substance and the first binding partner. When the first binding substance is a DNP group and the first binding partner is an anti-DNP antibody, it is preferred that the second binding substance is avidin or an avidin-like protein and the second binding partner is biotin.

When the labeling substance of the labeled antibody is an enzyme, the reagent kit of the present embodiment may further include a substrate of the enzyme. The substrate can be appropriately selected from substrates known in the art depending on the enzyme. When alkaline phosphatase is used as the enzyme, examples of the substrate include chemiluminescent substrates such as CDP-Star (registered trademark)(disodium 4-chloro-3-(methoxyspiro[1,2-dioxetane-3,2'-(5'-chloro)tricyclo[3.3.1.13,7]decan]-4-yl)phenyl phosphate) and CSPD (registered trademark)(disodium 3-(4-methoxyspiro[1,2-dioxetane-3,2-(5'-chloro)tricyclo [3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate, p-nitrophenyl phosphate and the like. In the case of using peroxidase as an enzyme, examples of the substrate include chromogenic substrates such as luminol and derivatives thereof, 2,2'-azinobis(3-ethylbenzothiazoline-6-sulfonic acid ammonium salt)(ABTS), 1,2-phenylenediamine (OPD), 3,3',5,5'-tetramethylbenzidine (TMB), and the like.

Figure 2C:
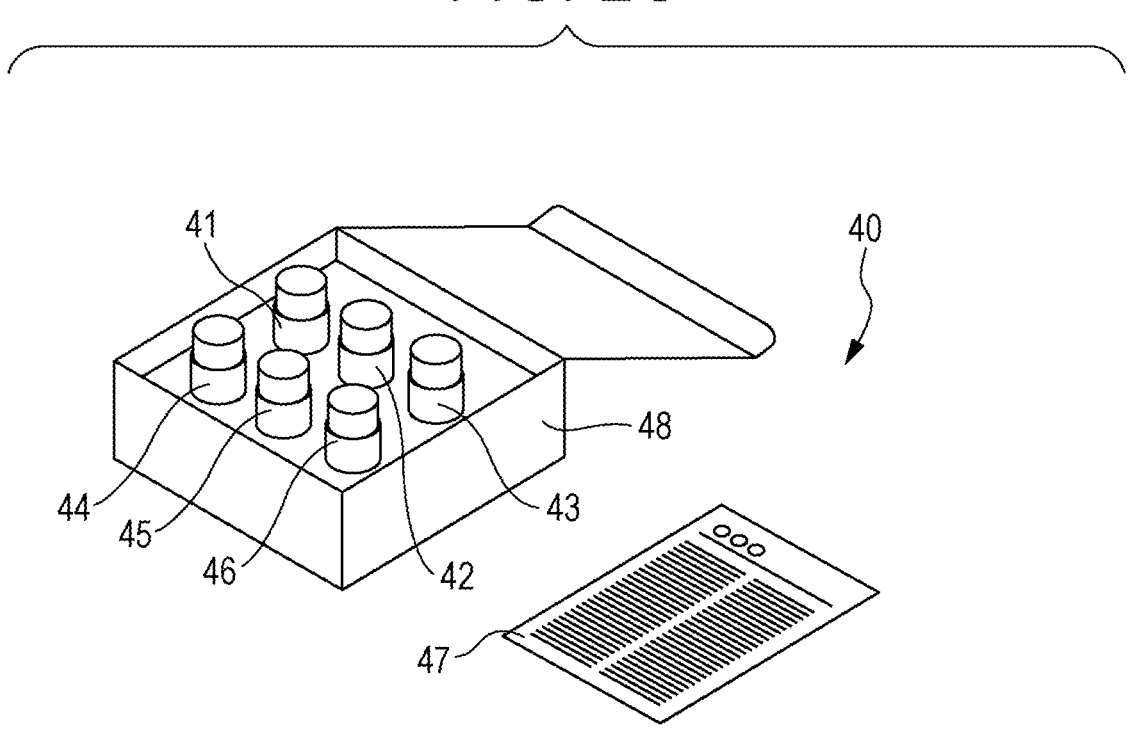
FIG. 2C is a schematic view showing an example of a reagent kit of the present embodiment.

An example of the antibody reagent kit of the present embodiment further including a substrate is shown in FIG. 2C. In FIG. 2C, a reference numeral 40 denotes a reagent kit, a reference numeral 41 denotes a first container containing the antibody reagent of the present embodiment, a reference numeral 42 denotes a second container containing a reagent including a capture substance capable of binding to the test substance, a reference numeral 43 denotes a third container containing a releasing agent, a reference numeral 44 denotes a fourth container containing a first solid phase as a particle, a reference numeral 45 denotes a fifth container containing a second solid phase as a particle, a reference numeral 46 denotes a sixth container containing a substrate, a reference numeral 47 denotes a package insert, and a reference numeral 48 denotes a packaging box.

Since the reagent kit of the present embodiment can realize an immune complex transfer method with high detection sensitivity, it is suitably used for detecting an HBs antigen. Therefore, the reagent kit of the present embodiment for detecting an HBs antigen in a sample by the ICT method comprises the antibody reagent of the present embodiment containing a labeled anti-HBs antibody and an anti-HBs antibody as a capture substance that binds to a site different from the site to which the labeled antibody contained in the antibody binds in the HBs antigen.

[3. Method for Producing Antibody Reagent]

The method for producing the antibody reagent of the present embodiment (hereinafter also referred to simply as "production method") will be described below. In the production method of the present embodiment, first, an antibody solution containing an antibody capable of binding to a test substance is brought into contact with a solid phase used for the immune complex transfer method. As described above, the antibody solution may contain a certain amount of an antibody non-specifically adsorbed to the solid phase. After bringing the antibody solution into contact with the solid phase, the solid phase and the antibody solution are separated, and the solution component is recovered, thereby to be able to remove the antibody that is non-specifically adsorbed onto the solid phase. Non-specific signals can be reduced by carrying out the ICT method using this solution component as an antibody reagent.

The antibody solution containing an antibody capable of binding to a test substance may be a solution containing an antibody which binds to a test substance by a specific antigen-antibody reaction to the test substance. Alternatively, a commercially available antibody solution may be used. The concentration of the antibody in the antibody solution is not particularly limited, but is usually 10 to 1000 ng/mL. The details of the type and origin of the antibody are the same as those described for the labeled antibody. The antibody capable of binding to the test substance may be labeled with a labeling substance. As the labeling substance, an enzyme and a fluorescent substance are preferable. The details of the labeling substance are as described above.

The antibody solution may contain one type of antibody or may contain two or more types of antibodies capable of binding to different test substances from each other. In the case where the antibody solution contains two or more types of antibodies, it is preferable that each antibody is an antibody which is labeled with a labeling substance generating detectable signals distinguishable from each other. Examples of such labeling substances are as described above.

The solid phase in contact with the antibody solution can be the first solid phase, the second solid phase, or both. When it is known in advance on which solid phase the antibody is non-specifically adsorbed, a solid phase onto which the antibody non-specifically adsorbs may be added. The solid phase is preferably capable of immobilizing the capture substance in the immune complex. On the solid phase, a binding substance for immobilizing the capture substance (preferably a capture antibody) may be immobilized. The details of such binding substances are similar to those described for the first binding substance. In the present embodiment, it is preferable that the solid phase is a magnetic particle having a first binding substance.

The operation of contacting the antibody solution with the solid phase can be appropriately determined depending on the shape of the solid phase. When the solid phase is in the form of a container such as a microplate, a microtube, a test tube or the like, placing an appropriate amount of antibody solution in a container as a solid phase brings the antibody solution into contact with the solid phase. When the solid phase is in the form of particles such as magnetic particles, the antibody solution and the solid phase are brought into contact with each other by adding particles to the antibody solution or mixing the antibody solution and the suspension of the particles. When the solid phase is a particle, the amount of the particle is not particularly limited, but for example, about 0.5 g of particles may be usually used per 1 mg of the antibody. The temperature and time at which the antibody solution and the solid phase are brought into contact with each other are not particularly limited, but the antibody solution and the solid phase may be incubated, for example, at 4 to 27° C. for 10 to 30 hours. During the incubation, stirring or shaking may be carried out.

In the production method of the present embodiment, the solid phase and the antibody solution in contact with the solid phase are then separated, and the antibody reagent of the present embodiment is prepared from the antibody solution in contact with the solid phase. A means for separating and collecting the antibody solution in contact with the solid phase from the solid phase can be appropriately determined depending on the shape of the solid phase. When the solid phase is in the shape of a container, the antibody solution contained in a container as a solid phase may be recovered. When the solid phase is in the form of particles, the supernatant may be separated and recovered from the mixture of the particles and the antibody solution. As a method for separating the supernatant, centrifugal separation, filtration and the like can be mentioned. When the solid phase is a magnetic particle, the supernatant is separated by collecting the magnetic particles with a magnet or a magnetism collector.

By separating the solid phase and the antibody solution in contact with the solid phase, an antibody that non-specifically binds or adsorbs to the solid phase is removed together with the solid phase from the antibody solution. Therefore, in the antibody solution separated from the solid phase, an antibody causing the non-specific signal is reduced. The antibody solution separated from the solid phase may be used as it is as the antibody reagent of the present embodiment. If necessary, the antibody solution separated from the solid phase may be subjected to treatments such as concentration, dilution, purification and lyophilization. In the case where the antibody is not labeled, the antibody contained in the recovered antibody solution may be labeled with a labeling substance.

As described above, in the production method of the present embodiment, after bringing the antibody solution and the solid phase into contact with each other, the antibody that non-specifically binds to the solid phase contained in the antibody solution is reduced by removing the solid phase, so that the antibody reagent of the present embodiment is obtained. In the antibody reagent obtained by the production method of the present embodiment, the ratio of the non-specific antibody is about $3.34 \times 10^{-7}$ or less (preferably $3.34 \times 10^{-7}$ or less). If necessary, for the antibody reagent obtained by the production method of the present embodiment, the ratio of non-specific antibody may be confirmed as described above.

The production method of the present embodiment is intended to be performed before detection of a test substance in a sample by the ICT method. That is, the step of mixing the sample, the antibody solution containing the antibody capable of binding to the test substance, and the solid phase in the ICT method does not correspond to the contacting step in the production method of the present embodiment. Therefore, in the production method of the present embodiment, the contacting step and the preparing step are performed before mixing the sample and the antibody solution.

In the case of producing an antibody reagent for detecting an HBs antigen in a sample by the ICT method according to the production method of the present embodiment, an antibody solution containing an anti-HBs antibody is used as an antibody solution, and a solid phase having a binding substance for immobilizing an anti-HBs antibody which binds to a site different from the site to which an anti-HBs antibody contained in the antibody solution is bound in the HBs antigen may be used as a solid phase used in the ICT method.

[4. Pretreatment of Antibody Solution]

The production method of the present embodiment can also be interpreted as a method for pretreating an antibody solution to obtain an antibody reagent capable of reducing non-specific signals in the ICT method. Therefore, the scope of the present disclosure includes a pretreatment method (hereinafter also simply referred to as "pretreatment method") of an antibody solution containing an antibody capable of binding to a test substance in a sample. The pretreatment of the antibody solution is intended to prepare the antibody reagent of the present embodiment by treating the antibody solution before detecting the test substance in the sample by the ICT method.

In the pretreatment method of the present embodiment, first, an antibody solution containing an antibody capable of binding to a test substance is brought into contact with a solid phase used in the ICT method. The details of antibody solution, solid phase and contact operation are the same as those described for the production method of the present embodiment. Next, the solid phase and the antibody solution in contact with the solid phase are separated, and from the antibody solution in contact with the solid phase, an antibody reagent for detecting a test substance in the sample is prepared by the ICT method. The details of the means for separating the solid phase and the antibody solution and the procedure for preparing the antibody reagent from the separated antibody solution are the same as those described for the production method of the present embodiment.

[5. Method for Detecting Test Substance]

The scope of the present disclosure also includes a method for detecting a test substance in a sample by the ICT method using the antibody reagent prepared by the production method of the present embodiment (hereinafter also simply referred to as "detection method"). The detection method of the present embodiment may be performed by a manual method or by using a fully automated immunoassay apparatus.

In the detection method of the present embodiment, first, an antibody reagent prepared by the production method of the present embodiment, a sample containing a test substance, a reagent containing a capture substance capable of binding to the test substance, and a first solid phase are mixed with each other. The order of mixing is not particularly limited. By mixing them, an immune complex comprising the labeled antibody contained in the antibody reagent, the test substance, and the capture substance is formed and the complex is immobilized on the first solid phase. The details of the antibody reagent, the sample containing the test substance, the reagent containing the capture substance capable of binding to the test substance, and the first solid phase are the same as those described above.

Depending on the type of the sample or the test substance, the pretreatment may be performed on the sample so as to be suitable for detection before mixing the sample and the various reagents. Such pretreatment is known in the art. For example, when the sample is a serum containing an HBs antigen, an endogenous antibody may be bound to the HBs antigen, so that the serum may be pretreated with a buffer solution containing an alkaline substance and a surfactant.

In the present embodiment, the capture substance is preferably an antibody having a first binding partner capable of binding to the first binding substance and a second binding partner capable of binding to the second binding substance. The first solid phase is preferably a magnetic particle to which the first binding substance is immobilized. The details of the binding substance and the binding partner are the same as those described for the reagent kit of the present embodiment. In the present embodiment, it is preferable that the first binding substance is an anti-DNP antibody, the first binding partner is a DNP group, and the second binding partner is biotin.

The temperature and reaction time in the step of immobilizing the immune complex on the first solid phase (immobilizing step) are not particularly limited, but may be incubated, for example, at 37 to 42° C. for 60 to 600 seconds. During the incubation, stirring or shaking may be carried out.

Next, free components not contained in the immune complex are removed from the mixture obtained in the immobilizing step. The step of removing this free component is carried out by separating the molecule immobilized on the solid phase (Bound) and the free molecule not immobilized on the solid phase (Free). Such separation is also called B/F separation. Examples of the free components not included in the immune complex include an unreacted labeled antibody, an unreacted capture substance, and a test substance not bound to the capture substance and the labeled antibody. The B/F separation can be carried out by a method known in the art. For example, when the first solid phase is a particle, the B/F separation can be carried out by centrifuging the mixture and removing the supernatant containing free components. In the case where the first solid phase is a magnetic particle, the B/F separation can be performed by collecting magnetic particles with a magnet or a magnetism collector and removing a liquid phase containing free components. If necessary, the first solid phase on which the immune complex is immobilized may be washed with an appropriate washing solution.

After removal of the free component, the immune complex is released from the first solid phase. This operation is preferably carried out by adding a releasing agent to dissociate the binding between the capture substance in the immune complex and the first solid phase. For example, when the capture substance in the immune complex and the first solid phase are bound by physical adsorption, the complex can be released by using a solution containing a surfactant as a releasing agent. In the case of ionic bonding, the complex can be released by using a solution containing ions. In the case where the capture substance in the immune complex and the first solid phase are bound via the first binding substance and the first binding partner, a releasing agent used in the reagent kit of the present embodiment may be preferably added. The temperature and reaction time in the step of releasing the immune complex from the first solid phase (releasing step) are not particularly limited, but the releasing step may be performed by, for example, incubation at 37 to 42° C. for 120 to 240 seconds. During the incubation, stirring or shaking may be carried out.

The immune complex released as described above is transferred onto a second solid phase different from the first solid phase. This operation is carried out by contacting the released immune complex with the second solid phase so that the immune complex is immobilized on the second solid phase. In the present embodiment, the second solid phase is preferably a magnetic particle to which the second binding substance is immobilized. The second binding substance is preferably avidin or an avidin-like protein.

In the step of transferring the released immune complex to the second solid phase (transfer step), the released immune complex is not intended to rejoin the first solid phase. Therefore, in the present embodiment, it is preferable to carry out B/F separation between the releasing step and the transfer step to recover a liquid phase containing the released immune complex. By bringing the recovered liquid phase into contact with the second solid phase, the immune complex can be transferred onto the second solid phase. The temperature and reaction time in the transfer step are not particularly limited, but the transfer step may be performed by, for example, incubation at 37° C. to 42° C. for about 240 seconds. During the incubation, stirring or shaking may be carried out.

After transferring the released immune complex to the second solid phase, a signal based on the labeled antibody contained in the immune complex on the second solid phase is measured, and the test substance is detected based on the signal. The "detecting a signal" means to qualitatively detect the presence or absence of a signal, quantify the amount or intensity of a signal, and to semi-quantitatively detect the signal in a plurality of stages of "no signal generation", "weak signal", and "strong signal". "Detecting a test substance" includes qualitative detection, quantitative detection, and semi-quantitative detection of a test substance according to the detection result of a signal. The semi-quantitative detection of a test substance refers to gradually indicating the amount or concentration of the test substance in a sample, such as "negative", "weak positive", "positive", and "strong positive".

Methods per se for detecting signals based on labeled antibodies are known in the art. The signal detection method can be appropriately selected according to the type of the labeling substance used for the labeled antibody. For example, in the case where the labeling substance is an enzyme, it can be carried out by measuring a signal such as light and color generated by reacting an enzyme with a substrate for the enzyme using a known measuring apparatus. As such a measuring apparatus, a spectrophotometer, a luminometer, or the like can be mentioned. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

In the present embodiment, in order to confirm the signal/noise ratio (S/N ratio) of detection, a sample not containing a test substance is subjected to a detection method, and a non-specific signal in the absence of the test substance may be quantitatively detected. This detection can be carried out as described above except that a sample not containing a test substance is used in place of a sample which may contain a test substance. If necessary, the background value by a reagent other than the antibody reagent of the present embodiment (for example, a substrate solution or the like) may also be measured. Such a background is also called a reagent blank.

In the detection method of the present embodiment, the first ratio shown in the following equation (1) may be calculated so as to ascertain to what extent the non-specific signal has been reduced.

$$\text{First ratio} = a/b \quad (1)$$

(wherein "a" is a non-specific signal value in the absence of the test substance and "b" is a signal value based on the labeled antibody in an amount used for one detection, contained in the antibody reagent.)

An antibody reagent in an amount used for one detection is an antibody reagent in an amount added to one sample in the above immobilizing step (hereinafter also referred to as "antibody reagent for one assay"). The signal value based on the labeled antibody contained in the antibody reagent for one assay can be measured as follows. When the labeling substance of the labeled antibody is an enzyme, the amount or intensity of the signal generated when reacting the antibody reagent for one assay with the substrate of the enzyme is quantitatively detected. When the labeling substance of the labeled antibody is a fluorescent dye, the antibody reagent for one assay is irradiated with an excitation light to quantitatively measure the intensity of the generated fluorescence.

The first ratio is a ratio of a signal value when measuring a sample containing no test substance to a signal value based on a labeled antibody in an amount used for one detection contained in the antibody reagent of the present embodiment. In the present embodiment, the value of the first ratio is usually about $1.02 \times 10^{-7}$ or less, preferably about $6.80 \times 10^{-8}$ or less. In a further embodiment, the value of the first ratio is $1.02 \times 10^{-7}$ or less, preferably $6.80 \times 10^{-8}$ or less. Since the first ratio is based on the signal values, it is possible to compare the reduction effect of non-specific signals between different assays.

In the detection method of the present embodiment, the second ratio shown in the following equation (2) may be calculated in order to ascertain to what extent the non-specific signal has been reduced.

$$\text{Second ratio} = a/c \quad (2)$$

(wherein "a" is a non-specific signal value in the absence of the test substance and "c" is a non-specific signal value in the absence of the test substance without the transfer step.)

The value of the non-specific signal in the absence of the test substance without the transfer step can be obtained as follows. First, a sample not containing a test substance is subjected to the immobilizing step and the free component removal step in the detection method of the present embodiment. Then, the first solid phase is recovered and a signal based on the labeled antibody non-specifically bound to the first solid phase is quantitatively detected. In other words, the value of "c" in the equation (2) is a non-specific signal value in the absence of the test substance in the immunological assay method not including the transfer step.

The second ratio is a ratio of the signal value when measuring a sample not containing a test substance to the non-specific signal value obtained by the measurement method not including the transfer step of an immune complex. The second ratio is an index showing to what extent the ICT method can reduce non-specific signals compared to the measurement method not including the immune complex transfer step. In the present embodiment, the value of the second ratio is usually about $4.68 \times 10^{-2}$ or less, preferably about $3.12 \times 10^{-2}$ or less. In a further embodiment, the value of the second ratio is equal to or less than $4.68 \times 10^{-2}$, preferably equal to or less than $3.12 \times 10^{-2}$. The smaller the value of the second ratio, the higher the reduction effect of the non-specific signal is, as compared with the measurement method not including the transfer step of the immune complex.

Hereinafter, the present invention will be described in detail with reference to Examples, but the present invention is not limited to these Examples. In addition, "HISCL" described below is a registered trademark of Sysmex Corporation.

EXAMPLES

Example 1: Preparation of Reagent Containing Labeled Antibody for Detection and Evaluation of Performance Thereof In Example 1, a solution containing a labeled antibody for detection was pretreated by bringing it into contact with a solid phase, thereby to prepare a reagent containing a labeled antibody for detection. For the obtained reagent, whether the non-specific reaction of the labeled antibody for detection to the solid phase was reduced was studied.

(1) Preparation of Labeled Antibody for Detection

Two anti-HBs antibody fragments labeled with alkaline phosphatase (ALP) were used as labeled antibodies for detection (hereinafter referred to as "ALP labeled HBs 149 Fab'" and "ALP labeled HBs 85 Fab'", respectively). The ALP labeled HBs 149 Fab' was prepared from monoclonal antibodies produced by the hybridoma deposited under accession number FERM BP-10583 on Mar. 27, 2006 at the National Institute of Technology and Evaluation, Patent Microorganisms Depository (ZIP Code 292-0818, Kazusakamatari 2-5-8, Kisarazu-shi, Chiba, Japan). The ALP labeled HBs 85 Fab' was prepared from monoclonal antibodies produced by the hybridoma deposited under accession number NITE BP-1483 on Dec. 13, 2012 at the National Institute of Technology and Evaluation, Patent Microorganisms Depository (ZIP Code 292-0818, Kazusakamatari 2-5-8, Kisarazu-shi, Chiba, Japan). A specific procedure for preparing a labeled antibody for detection is as follows. Each monoclonal antibody was digested with pepsin and reduced to obtain a Fab' fragment. In addition, ALP (Oriental Yeast Co., Ltd.) was maleimidated using EMCS (N-(6-maleimidocaproyloxy)succinimide) (Dojindo Laboratories). Then, the resulting Fab' fragment was mixed with the maleimidated ALP and reacted to obtain a labeled antibody for detection (Fab'-ALP). The resulting labeled antibody for detection was diluted with a diluent (0.1 M MES (pH 6.5), 0.15 M NaCl, 1.0% BSA, 0.1% NaN$_3$, 10 mM MgCl$_2$ and 1 mM ZnCl$_2$). A solution (ALP concentration 10 pmol/mL) containing a labeled antibody for detection was prepared by mixing each labeled antibody for detection and a diluent at a ratio of 1:1. Hereinafter, the obtained solution is also referred to as "antibody reagent without pretreatment".

(2) Preparation of Anti-DNP Antibody-Immobilized Magnetic Particles

Anti-DNP antibody (DNP-1753) was immobilized on the surface of magnetic particles (Micromer M, manufactured by Micromod Company) to obtain a first solid phase. The obtained first solid phase was diluted with a diluent (0.1 M MES (pH 6.5), 0.15 M NaCl, 0.25% BSA and 0.1% NaN$_3$) to prepare a solution containing anti-DNP antibody-immobilized magnetic particles (particle concentration 1.0%). Immobilization of the antibody to the magnetic particles was carried out using Sulfo-SMCC (Pierce Co., Ltd.). The above-mentioned DNP-1753 antibody is a monoclonal antibody produced by the hybridoma deposited under accession number NITE P-845 on Nov. 25, 2009 at the National Institute of Technology and Evaluation, Patent Microorganisms Depository.

(3) Preparation of Reagent Containing Labeled Antibody for Detection (Pretreatment of Antibody Solution)

The solution (10 µL) containing the anti-DNP antibody-immobilized magnetic particles obtained in the above (2) was added to 500 µL of the solution containing the labeled antibody for detection obtained in the above (1), and the resulting solution was subjected to inversion-stirring at 4° C. overnight. Thereafter, the magnetic particles in the solution were magnetically collected using a magnet, and only the supernatant was recovered to remove the magnetic particles from the solution. Hereinafter, the obtained supernatant was used as a reagent containing a labeled antibody for detection (hereinafter also referred to as "pretreated antibody reagent").

(4) Relation Between Amount of Labeling Substance in Labeled Antibody for Detection and Signal Value In the labeled antibody for detection of Example 1, the antibody fragment and the labeling substance (ALP) are covalently bonded. Therefore, the amount of ALP in the pretreated antibody reagent reflects the number of molecules of the labeled antibody for detection contained in the reagent. The signal value of chemiluminescence generated by the reaction between ALP and the substrate reflects the amount of ALP used in the reaction when the amount of substrate is constant. Therefore, in order to calculate, based on the signal value, the ratio of the number of molecules of the labeled antibody for detection involved in the non-specific reaction, a coefficient representing the relationship between the number of moles of ALP in the reagent containing the labeled antibody for detection and the signal value (hereinafter also referred to as "conversion coefficient") was calculated as follows. Note that this coefficient corresponds to the conversion coefficient described in the explanation of the antibody reagent of the present embodiment.

(4-1) Reagents and Measuring Apparatus r3 Reagent: Reagent containing the labeled antibody for detection obtained in the above (3)

Buffer for activating ALP: 0.1 M MES (pH 6.5), 0.15 M NaCl, 0.25% BSA and 0.1% NaN$_3$ Buffer for luminescent substrate: HISCL R4 reagent (Sysmex Corporation)

Luminescent substrate: HISCL R5 reagent (CDP-Star (registered trademark)) (Sysmex Corporation)

Measuring apparatus: Fully automated immunoassay apparatus HISCL-800 (Sysmex Corporation)

(4-2) Measurement Procedure

The following operation was performed by HISCL-800 (Sysmex Corporation). The r3 reagent was diluted with the buffer for activating ALP to a concentration of 1/1000 (1000-fold dilution). The HISCL-800 was set to ALP activation mode, and the diluted r3 reagent (20 µL), the HISCL R4 reagent (50 µL) and the HISCL R5 reagent (100 µL) were mixed. Then, the HISCL-800 was set to ICT measurement mode, and the resulting mixture was incubated at 42° C. for 5 minutes, and the emission intensity was measured as a signal value.

(4-3) Result

The emission intensity obtained by the above measurement was 3,997,991 counts. This value is obtained from the reaction between ALP of the labeled antibody for detection contained in the r3 reagent (20 µL) diluted 1000 times and the substrate. This value was multiplied by the dilution ratio (1000 times) to calculate 3,997,991,000 counts. The calculated value is a theoretical value of the emission intensity obtained when ALP of all the labeled antibodies for detection contained in the r3 reagent (20 µL) before dilution is reacted with the substrate. Next, the number of moles of ALP in the r3 reagent (20 µL) before dilution was calculated as follows. The ALP concentration of the reagent containing the labeled antibody for detection obtained in the above (3) was set to 10 pmol/mL which was the same as the ALP concentration of the solution containing the labeled antibody for detection obtained in the above (1). Therefore, the number of moles of ALP contained in the r3 reagent (20 µL) is 200 fmol (10 pico mol/mL×20 µL=200 femto mol). The above signal value was divided by the number of moles of ALP to calculate "20 counts/zmol" as a conversion coefficient (3,997,991,000 counts/200 fmol=about 20 counts/zepto mol).

(5) Study of Non-Specific Signals Using Reagent Containing Labeled Antibody for Detection (5-1) Samples, Reagents and Measuring Apparatus Sample: HISCL HBsAg calibrator (HBs antigen concentration 0 IU/mL) (Sysmex Corporation)

Buffer for sample treatment: 0.1 M MES (pH 6.5), 1.0% BSA, 10 mM MgCl$_2$ and 1 mM ZnCl$_2$ r3 reagent: Reagent containing the labeled antibody for detection obtained in the above (3)

r5 reagent (first solid phase): Solution containing the anti-DNP antibody-immobilized magnetic particles obtained in the above (2)

Washing solution: HISCL washing solution (Sysmex Corporation)

Buffer for substrate: HISCL R4 reagent (Sysmex Corporation)

Luminescent substrate: HISCL R5 reagent (CDP-Star (registered trademark)) (Sysmex Corporation)

Measuring apparatus: Fully automated immunoassay apparatus HISCL-800 prototype (Sysmex Corporation)

(5-2) Measurement Procedure

The following operation was performed by the HISCL-800 prototype (Sysmex Corporation). A sample (70 µL) and the buffer (60 µL) for sample treatment were mixed and incubated at 42° C. for 72 seconds. The r3 reagent (20 µL) was added to the resulting mixture and the mixture was incubated at 42° C. for 584 seconds. The r5 reagent (20 µL) was added to the resulting mixture and incubation was performed at 42° C. for 720 seconds. The magnetic particles in the obtained mixed solution were collected to remove the supernatant, and the HISCL washing solution (300 μL) was added to wash the magnetic particles (B/F separation). The B/F separation was performed three more times. The supernatant was removed and the HISCL r4 reagent (50 μL) and the HISCL R5 reagent (100 μL) were added to the magnetic particles. The resulting mixture was incubated at 42° C. for 300 seconds, and the emission intensity was measured. The value of the reagent blank was measured in the same manner as above, except that the r3 reagent was not added. In the same manner as described above except that a solution (20 μL) containing the labeled antibody for detection obtained in the above (1) was used in place of the r3 reagent, the emission intensity of the antibody reagent without pretreatment was measured for comparison.

(5-3) Result

The value of the reagent blank (360 counts) was subtracted from the measured signal value to obtain a net signal value. Since the sample used in Example 1 does not contain an HBs antigen as the test substance, the obtained value shows an emission intensity derived from the labeled antibody for detection non-specifically bound to the first solid phase. The net signal value was divided by the conversion coefficient (20 counts/zmol) to calculate the number of moles of ALP of the labeled antibody for detection non-specifically bound to the first solid phase. Here, the ALP concentrations in the r3 reagent and the antibody reagent without pretreatment are all 10 pmol/mL. Therefore, the number of moles of ALP in the antibody reagent for one assay (20 μL) is 200 fmol. The number of moles of ALP is a value that reflects the number of molecules of the labeled antibody for detection. Using these values, the ratio of the number of molecules of the labeled antibody for detection non-specifically reacting with the first solid phase to the number of molecules of the labeled antibody for detection contained in the reagent containing the antibody for detection was calculated as a molar ratio of ALP. Each value is shown in Table 1. In Table 1, "Ave." indicates the average value of two values.

TABLE 1

|  | Signal value (counts) | Net signal value (counts) | Number of moles of ALP (zmol) | Ratio of molecules of antibody (molar ratio of ALP) |
|---|---|---|---|---|
| Pretreated antibody reagent | 1696 | 1336 | 67 | $3.35 \times 10^{-7}$ |
|  | 1483 | 1123 | 56 | $2.80 \times 10^{-7}$ |
|  | (Ave. 1590) | (Ave. 1230) | (Ave. 62) | (Ave. $3.07 \times 10^{-7}$) |
| Antibody reagent without pretreatment | 1778 | 1418 | 71 | $3.55 \times 10^{-7}$ |
|  | 1842 | 1482 | 74 | $3.70 \times 10^{-7}$ |
|  | (Ave. 1810) | (Ave. 1450) | (Ave. 73) | (Ave. $3.63 \times 10^{-7}$) |

As shown in Table 1, the signal value when using the pretreated antibody reagent was lower than the signal value when using the antibody reagent without pretreatment. In addition, regarding the ratio of the number of molecules of the labeled antibody for detection non-specifically reacting with the first solid phase to the number of molecules of the labeled antibody for detection contained in the antibody reagent for detection, such a ratio in the pretreated antibody reagent was lower than that in the untreated antibody reagent. Therefore, it was shown that non-specific signals derived from non-specific binding of the labeled antibody for detection can be reduced by the pretreatment of bringing the antibody reagent for detection into contact with the solid phase.

Example 2: Immune Complex Transfer Method Using Reagent Containing Labeled Antibody for Detection An HBs antigen was measured by the ICT-EIA method using the reagent containing a labeled antibody for detection prepared in Example 1 (pretreated antibody reagent). For comparison, HBs antigen was similarly measured using the antibody reagent without pretreatment prepared in Example 1.

(1) Sample, Reagent and Measuring Apparatus

Sample: HISCL HBsAg calibrator (HBs antigen concentration 0 IU/mL and 0.25 IU/mL) (Sysmex Corporation)

Solution for sample pretreatment: 0.3 N NaOH, 5 mM $NaH_2PO_4$, 25 mM $Na_2HPO_4$, 2.4 M urea and 0.8% Brij (registered trademark) 35

Neutralizing solution: 0.1 M citric acid, 20 mM mercaptoethylamine, 20 mM NaCl and 0.1% $NaN_3$ r3 reagent (antibody for detection): reagent containing the labeled antibody for detection obtained in Example 1 r4 reagent (capture antibody): reagent containing an anti-HBs Ag antibody fragment (Fab'-BSA-Bio-DNP) modified with biotin and DNP (this reagent was prepared by the procedure described in WO 2014/115878 A1)

r5 reagent (first solid phase): solution containing the anti-DNP antibody-immobilized magnetic particles obtained in Example 1 r6 reagent (releasing agent): 5 mM N-(2,4-dinitrophenyl)-L-lysine (DNP-Lys), 0.1 M MES (pH 6.5), 2% casein sodium and 0.1% $NaN_3$ r7 reagent (second solid phase): solution containing magnetic particles immobilized with streptavidin (MAG2201, JSR Corporation)

Washing solution: HISCL washing solution (Sysmex Corporation)

Buffer for substrate: HISCL R4 reagent (Sysmex Corporation)

Luminescent substrate: HISCL R5 reagent (CDP-Star (registered trademark)) (Sysmex Corporation)

Measuring apparatus: Fully automated immunoassay apparatus HISCL-800 (Sysmex Corporation)

(2) Measurement Procedure

The following operation was performed by HISCL-800 (Sysmex Corporation). The sample (70 μL) and the pretreated sample solution (20 μL) were mixed and incubated at 42° C. for 504 seconds. The neutralizing solution (20 μL) was added thereto and the mixture was incubated at 42° C. for 72 seconds. The r4 reagent (20 μL) was added to the resulting mixture and incubated at 42° C. for 216 seconds. The r3 reagent (20 μL) was added to the resulting mixture and incubated at 42° C. for 584 seconds to form an immune complex comprising an HBs antigen, a labeled antibody for detection, and a capture antibody. The r5 reagent (20 μL) was added to the immune complex and the immune complex was captured on the first solid phase by incubating it at 42° C. for 720 seconds. The magnetic particles in the resulting mixed solution were collected to remove the supernatant, and the HISCL washing solution (300 μL) was added to wash the magnetic particles (B/F separation). The B/F separation was performed three more times. The supernatant was removed, and the r6 reagent (41 μL) was added to the magnetic particles, followed by incubation at 42° C. for 144 seconds to release the captured immune complex on the first solid phase into the solution. The supernatant (30 μL) was collected and transferred to another cuvette. The r7 reagent (30 µL) was added to the cuvette and incubated at 42° C. for 288 seconds to capture the immune complex on the second solid phase (transfer of immune complex). The magnetic particles in the obtained mixed solution were collected to remove the supernatant, and the HISCL washing solution (300 µL) was added to wash the magnetic particles (B/F separation). The B/F separation was performed three more times. The supernatant was removed and the HISCL R4 reagent (50 µL) and the HISCL R5 reagent (100 µL) were added to the magnetic particles. The resulting mixture was incubated at 42° C. for 300 seconds, and the emission intensity was measured. For comparison, in the same manner as described above except that the solution (20 µL) containing the labeled antibody for detection obtained in Example 1 was used in place of the r3 reagent, the emission intensity when using the antibody reagent without pretreatment was measured. In addition, the r7 reagent (30 µL), the HISCL R4 reagent (50 µL) and the HISCL R5 reagent (100 µL) were mixed and the emission intensity was measured to obtain a value of the reagent blank.

(3) Result

The value of the reagent blank (434 counts) was subtracted from the measured signal value to obtain a net signal value. The signal value obtained by measuring a sample with an HBs antigen concentration of 0 IU/mL is a measurement value of a sample not containing a test substance, which corresponds to a noise due to a non-specific reaction of the labeled antibody for detection. From the obtained signal value, the S/N ratio was calculated by the following equation. The net signal value (counts) and the S/N ratio are shown in Table 2.

S/N ratio=[(Signal value of sample with HBs antigen concentration of 0.25 IU/mL)−(Signal value of sample with HBs antigen concentration of 0 IU/mL)]/(Signal value of sample with HBs antigen concentration of 0 IU/mL)

TABLE 2

|  | HBs antigen (IU/mL) | | S/N ratio |
|---|---|---|---|
|  | 0 | 0.25 |  |
| Pretreated antibody reagent | 128 | 119358 | 931 |
| Antibody reagent without pretreatment | 484 | 118255 | 243 |

As shown in Table 2, with respect to the sample with the HBs antigen concentration of 0 IU/mL, the signal value when using the pretreated antibody reagent was reduced to about ¼ of the signal value when using the antibody reagent without pretreatment. Therefore, it was shown that non-specific signals derived from non-specific binding of the labeled antibody for detection can be reduced in the immune complex transfer method by pretreating the antibody reagent for detection through contact with the solid phase. On the other hand, for the sample with HBs antigen concentration of 0.25 IU/mL, no significant change in signal value was observed. This suggests that the pretreatment of the antibody reagent for detection does not affect the detection performance of the test substance. As a result, the pretreatment of the antibody reagent for detection greatly reduces the noise without affecting the signal, so that the S/N ratio is markedly improved. As shown in Table 2, the S/N ratio when the pretreated antibody reagent was used was about 4 times higher than the S/N ratio when the antibody reagent without pretreatment was used.

Example 3: Evaluation of Reduction Effect of Non-Specific Signal (1)

The effect of reducing the non-specific signal by the detection method of the test substance of the present embodiment was evaluated based on the signal value.

Specifically, the first ratio was calculated using the signal values obtained in Examples 1 and 2, and the reduction effect of the non-specific signals was evaluated based on the calculated values. The first ratio is a signal value ratio when measuring a sample not containing a test substance to the signal value based on the labeled antibody for detection contained in the antibody reagent for detection in an amount used for one detection (one assay amount). Hereinafter, the first ratio is also referred to as "non-specific ratio (X)". In Example 3, the non-specific ratio (X) was calculated by the following equation:

(Non-specific ratio(X))=[(Signal value of sample with HBs antigen concentration of 0 IU/mL)−(Reagent blank value)]/(Signal value based on ALP-labeled antibody contained in 20 µL of r3 reagent)

According to Example 1, the signal value derived from all the labeled antibodies for detection contained in 20 µL of the r3 reagent (antibody reagent for detection in one assay) was 3,997,991,000 counts. In addition, according to Example 2, the signal value of the sample with HBs antigen concentration of 0 IU/mL, obtained by subtracting the reagent blank value, was found to be 128 counts. Therefore, the non-specific ratio (X) of the ICT-EIA method using the pretreated antibody reagent was $3.2 \times 10^{-8}$ (128/399799100=about $3.2 \times 10^{-8}$). Similarly, when calculating the non-specific ratio (X) of the ICT-EIA method using the antibody reagent without pretreatment, it was found to be $12.1 \times 10^{-8}$ (484/3997991000=about $12.1 \times 10^{-8}$). The non-specific ratio (X) when using the pretreated antibody reagent was reduced to about ¼ of the non-specific ratio (X) when using the antibody reagent without pretreatment.

By comparing the non-specific ratio (X), it is found that the non-specific signal reduction effect when using the pretreated antibody reagent is about 4 times higher than when using the antibody reagent without pretreatment. As mentioned above, since the non-specific ratio (X) is based on the signal value, it is possible to compare the reduction effect of non-specific signals among different assays.

Reference Example: Effect of Pretreatment of Antibody Reagent for Detection in Measurement Method without Immune Complex Transfer Step An examination was made as to whether the reduction effect of non-specific signals was observed similarly to the ICT-EIA method when using the pretreated antibody reagent in the measurement method (sandwich immunoassay method) not including the immune complex transfer step.

(1) Sample, Reagent and Measuring Apparatus

Sample: HISCL HBsAg calibrator (HBs antigen concentrations 0 IU/mL and 0.25 IU/mL) (Sysmex Corporation)

Solution for sample pretreatment: 0.3 N NaOH, 5 mM $NaH_2PO_4$, 25 mM $Na_2HPO_4$, 2.4 M urea and 0.8% Brij (registered trademark) 35

Neutralizing solution: 0.1 M citric acid, 20 mM mercaptoethylamine, 20 mM NaCl and 0.1% $NaN_3$ r3 reagent (antibody for detection): a reagent containing the labeled antibody for detection obtained in Example 1 r4 reagent (capture antibody): the same reagent as in Example 2 (reagent containing Fab'-BSA-Bio-DNP)

r5 reagent (first solid phase): a solution containing the anti-DNP antibody-immobilized magnetic particles obtained in Example 1

Washing solution: HISCL washing solution (Sysmex Corporation)

Buffer for substrate: HISCL R4 reagent (Sysmex Corporation)

Luminescent substrate: HISCL R5 reagent (CDP-Star (registered trademark)) (Sysmex Corporation)

Measuring apparatus: Fully Automated immunoassay system HISCL-800 (Sysmex Corporation)

(2) Measurement Procedure

The following operation was performed by using HISCL-800 (Sysmex Corporation). The sample (70 µL) and the solution for sample pretreatment (20 µL) were mixed and incubated at 42° C. for 504 seconds. The neutralizing solution (20 µL) was added thereto, and the mixture was incubated at 42° C. for 72 seconds. The r4 reagent (20 µL) was added to the resulting mixture and incubated at 42° C. for 216 seconds. The r3 reagent (20 µL) was added to the resulting mixture and incubated at 42° C. for 584 seconds to form an immune complex containing the HBs antigen, the labeled antibody for detection, and the capture antibody. The r5 reagent (20 µL) was added to the immune complex and the immune complex was captured on the first solid phase by incubating it at 42° C. for 720 seconds. The magnetic particles in the resulting mixed solution were collected to remove the supernatant, and the HISCL washing solution (300 µL) was added to wash the magnetic particles (B/F separation). The B/F separation was performed three more times. The supernatant was removed, and the HISCL R4 reagent (50 µL) and the HISCL R5 reagent (100 µL) were added to the magnetic particles. The resulting mixture was incubated at 42° C. for 300 seconds and the emission intensity was measured. For comparison, the emission intensity when using the antibody reagent without pretreatment was measured in the same manner as described above except that the solution (20 µL) containing the labeled antibody for detection obtained in Example 1 was used in place of the r3 reagent. In addition, the r5 reagent (20 µL), the HISCL R4 reagent (50 µL) and the HISCL R5 reagent (100 µL) were mixed and the emission intensity was measured to obtain a value of the reagent blank.

(3) Results

A net signal value was obtained by subtracting the value of the reagent blank from the measured signal value. From the obtained signal value, the S/N ratio was calculated in the same manner as in Example 2. The net signal value (counts) and the S/N ratio are shown in Table 3.

TABLE 3

| | HBs antigen (IU/mL) | | |
|---|---|---|---|
| | 0 | 0.25 | S/N ratio |
| Pretreated antibody reagent | 3269 | 328457 | 99 |
| Antibody reagent without pretreatment | 3996 | 341250 | 84 |

As shown in Table 3, with respect to the sample having an HBs antigen concentration of 0 IU/mL, the signal value when using the pretreated antibody reagent was lower than the signal value when using the antibody reagent without pretreatment. However, the S/N ratio was not improved much. Therefore, it was found that even if the pretreated antibody reagent was used in the sandwich immunoassay method, the effect of reducing non-specific signal to such an extent as to remarkably improve the S/N ratio was not observed. That is, it was shown that the effect of the pretreatment of the antibody reagent for detection is exerted more remarkably in the immune complex transfer method.

Example 4: Evaluation of Reduction Effect of Non-Specific Signal (2)

The effect of reducing the non-specific signal by the detection method of the test substance according to the present embodiment was evaluated on the basis of the comparison with the value of the non-specific signal obtained by the measurement method not including the immune complex transfer step. Specifically, the second ratio was calculated using the signal values obtained in Example 2 and Reference Example, and the reduction effect of the non-specific signal was evaluated based on the calculated value. The second ratio is a ratio of a signal value when a sample not containing a test substance is measured to a value of a non-specific signal obtained by a measurement method not including a transfer step of an immune complex. Hereinafter, the second ratio is also referred to as "non-specific ratio (Y)". In Example 4, the non-specific ratio (Y) was calculated by the following equation (Non-specific ratio($Y$))=[(Signal value of sample with HBs antigen concentration of 0 IU/mL)−(Reagent blank value)]/(Signal value of sample with HBs antigen concentration 0 IU/mL by sandwich immunoassay)

From the Reference Example, the signal values of the sample with the HBs antigen concentration of 0 IU/mL by the sandwich immunoassay were found to be 3269 and 3996 counts. In Example 4, the average value (3633 counts) of these signal values was used. In addition, according to Example 2, the signal value of the sample with the HBs antigen concentration of 0 IU/mL, obtained by subtracting the value of the reagent blank, was found to be 128 counts. Therefore, the non-specific ratio (Y) of the ICT-EIA method using the pretreated antibody reagent was $3.5 \times 10^{-2}$ (128/3633=about $3.5 \times 10^{-2}$). Similarly, when calculating the non-specific ratio (Y) of the ICT-EIA method using the antibody reagent without pretreatment, it was found to be $13.4 \times 10^{-2}$ (484/3633=about $13.4 \times 10^{-2}$).

The non-specific ratio (Y) is an index showing how much the non-specific signal can be reduced by the immune complex transfer method compared to the measurement method not including the immune complex transfer step. The smaller the value of the non-specific ratio (Y), the higher the reduction effect of the non-specific signal, when compared to the measurement method not including the transfer step of the immune complex. Since the non-specific ratio (Y) of the ICT-EIA method using the antibody reagent without pretreatment was $13.4 \times 10^{-2}$, it can be said that the reduction effect of the non-specific signal in this method is higher than the sandwich immunoassay, as conventionally known. On the other hand, the non-specific ratio (Y) of the ICT-EIA method using the pretreated antibody reagent was $3.5 \times 10^{-2}$. Therefore, it can be understood that the detection method according to the present embodiment has a higher effect of reducing non-specific signals more than the ICT-EIA method using an antibody reagent without pretreatment.

What is claimed is:

1. A method for purifying an antibody reagent and detecting a test substance in a sample by an immune complex transfer method by use of the purified antibody reagent, comprising the steps of:
provide an antibody solution comprising labeled antibodies prepared by complexing a label and Fab' fragment of a monoclonal antibody, the labeled antibodies being capable of binding to the test substance;
bringing the antibody solution into contact with a first solid phase and/or a second solid phase which are used in the immune complex transfer method, under absence of the test substance derived from a sample, whereby preparing a mixture comprising: the labeled antibody which nonspecifically binds to the solid phase; and the labeled antibody which does not bind to the solid phase, wherein the first solid phase comprises a first binding substance and the second solid phase comprises a second binding substance;
removing from the mixture the solid phase with the labeled antibodies which are non-specifically bound to the solid phase and retrieving the solution comprising the labeled antibodies which are not bound to the solid phase as the antibody reagent;
mixing (i) the antibody reagent, (ii) a sample comprising the test substance, (iii) a reagent comprising a capture substance capable of binding to the test substance and comprising a first binding partner capable of binding to the first binding substance and a second binding partner capable of binding to the second binding substance, and (iv) the first solid phase, and thereby forming an immune complex comprising the labeled antibody, the test substance, the capture substance and the first solid phase;
removing a free component not contained in the immune complex from the mixture;
releasing the immune complex from the first solid phase;
transferring the released immune complex onto the second solid phase, and
detecting a signal based on the labeled antibody comprised in the immune complex on the second solid phase and detecting the test substance based on the signal.

2. The method according to claim 1, wherein the ratio of the number of molecules of the labeled antibody which can non-specifically bind to a solid phase used in the immune complex transfer method to the number of molecules of the labeled antibody comprised in the antibody reagent is about $3.34 \times 10^{-7}$ or less.

3. The method according to claim 1, wherein the first solid phase or the second solid phase is coated with a hapten or an anti-hapten antibody, and the anti-hapten antibody is an antibody specifically binding to a dinitrophenyl (DNP) group, and the hapten is a DNP group.

4. The method according to claim 1, wherein the solid phase is magnetic particles.

* * * * *